United States Patent
Cho et al.

(10) Patent No.: US 10,125,023 B2
(45) Date of Patent: Nov. 13, 2018

(54) MANUFACTURING METHOD OF MESOPOROUS INORGANIC OXIDE AND MESOPOROUS INORGANIC OXIDE MADE BY THE SAME

(71) Applicant: INDUSTRY FOUNDATION OF CHONNAM NATIONAL UNIVERSITY, Gwangju (KR)

(72) Inventors: Sung June Cho, Gwangju (KR); Hyun Jeong Lee, Gyeonggi-do (KR)

(73) Assignee: INDUSTRY FOUNDATION OF CHONNAM NATIONAL UNIVERSITY, Gwangju (KR)

( * ) Notice: Subject to any disclaimer, the term of this patent is extended or adjusted under 35 U.S.C. 154(b) by 0 days.

(21) Appl. No.: 14/891,195

(22) PCT Filed: Sep. 23, 2015

(86) PCT No.: PCT/KR2015/009988
§ 371 (c)(1),
(2) Date: Nov. 13, 2015

(87) PCT Pub. No.: WO2016/085104
PCT Pub. Date: Jun. 2, 2016

(65) Prior Publication Data
US 2017/0305754 A1    Oct. 26, 2017

(30) Foreign Application Priority Data
Nov. 25, 2014  (KR) .................. 10-2014-0164980
May 12, 2015   (KR) .................. 10-2015-0066276

(51) Int. Cl.
B01J 23/02    (2006.01)
B01J 23/06    (2006.01)
(Continued)

(52) U.S. Cl.
CPC .............. *C01F 5/02* (2013.01); *B01D 53/02* (2013.01); *B01D 53/04* (2013.01); *B01J 20/041* (2013.01);
(Continued)

(58) Field of Classification Search
CPC .... C01F 5/02; B01J 20/28007; B01J 20/3078; B01J 20/364; B01J 20/28073;
(Continued)

(56) References Cited

U.S. PATENT DOCUMENTS 7,985,400 B2 *  7/2011  Shan .................. B01J 21/08
                                          423/702

FOREIGN PATENT DOCUMENTS

JP    2009007192 A    1/2009
KR  10-1996-0016589 B1  12/1996
(Continued)

OTHER PUBLICATIONS

A.Tadjarodi, Synthesis and Charaterization of Magensium Oxide Mesoporous Microstructures Using Pluronic F127, Journal of Nanostructures; Jan. 12, 2012, pp. 273-278.
(Continued)

*Primary Examiner* — Haytham Soliman
(74) *Attorney, Agent, or Firm* — Saliwanchik, Lloyd & Eisenschenk

(57) ABSTRACT

Provided is a method for manufacturing a mesoporous inorganic oxide, which includes preparing a mixture of a metal salt selected from the group consisting of at least one kind of alkali metal-containing compound, at least one kind of alkaline earth metal-containing compound, and any combination thereof and an amorphous inorganic oxide; sintering the mixture of a metal salt and an amorphous inorganic oxide; and removing the metal salt contained in the sintered mixture, and a mesoporous inorganic oxide that is manu-
(Continued)

factured by the above method and is composed of an aggregate of inorganic oxide particles having a size of from 2 nm to 5 nm.

According to the present invention, it is possible to provide a method for manufacturing a mesoporous inorganic oxide which has a simplified manufacturing process, has a short period of manufacturing time of about 1 day, does not generate secondary environmental contaminants to be environmentally friendly, and enables mass production, and a mesoporous inorganic oxide which has a dramatically decreased particle size and thus has an increased specific surface area and increased active sites.

17 Claims, 7 Drawing Sheets

(51) Int. Cl.
*C01F 5/02* (2006.01)
*B01D 53/04* (2006.01)
*B01J 20/04* (2006.01)
*B01J 20/28* (2006.01)
*B01J 20/30* (2006.01)
*B01J 35/00* (2006.01)
*B01J 35/10* (2006.01)
*B01J 37/00* (2006.01)
*B01J 37/04* (2006.01)
*B01J 37/08* (2006.01)
*C07C 253/30* (2006.01)
*B01D 53/02* (2006.01)

(52) U.S. Cl.
CPC ... *B01J 20/28007* (2013.01); *B01J 20/28016* (2013.01); *B01J 20/28061* (2013.01); *B01J 20/28071* (2013.01); *B01J 20/28073* (2013.01); *B01J 20/3064* (2013.01); *B01J 20/3078* (2013.01); *B01J 23/02* (2013.01); *B01J 35/0013* (2013.01); *B01J 35/1019* (2013.01); *B01J 35/1038* (2013.01); *B01J 35/1042* (2013.01); *B01J 37/0018* (2013.01); *B01J 37/04* (2013.01); *B01J 37/08* (2013.01); *C07C 253/30* (2013.01); *B01D 2253/1124* (2013.01); *B01D 2253/304* (2013.01); *B01D 2253/306* (2013.01); *B01D 2253/311* (2013.01); *B01D 2257/504* (2013.01); *B01D 2258/06* (2013.01); *C01P 2002/72* (2013.01); *C01P 2004/03* (2013.01); *C01P 2004/64* (2013.01); *C01P 2006/12* (2013.01); *C01P 2006/14* (2013.01)

(58) Field of Classification Search
CPC .......... B01J 20/28071; B01J 20/28061; B01J 20/28016; B01J 20/041; B01J 37/08; B01J 37/04; B01J 37/0018; B01J 35/1042; B01J 35/1038; B01J 35/1019; B01J 35/0013; B01J 23/02; C07C 253/30; B01D 53/04; B01D 2253/1124; B01D 2257/504; B01D 2253/306; B01D 2253/311; C01P 2002/72; C01P 2004/03; C01P 2006/14; C01P 2006/12; C01P 2004/64
USPC .......................................................... 502/340
See application file for complete search history.

(56) References Cited

FOREIGN PATENT DOCUMENTS

| KR | 10-2001-0086695 A | 9/2001 |
| KR | 10-2006-0011738 A | 2/2006 |
| KR | 10-2006-0079588 A | 7/2006 |
| KR | 1020080078864 A | 8/2008 |
| KR | 10-2010-0064101 A | 6/2010 |

OTHER PUBLICATIONS

International Search Report in International Application No. PCT/KR2015/009988, filed Sep. 23, 2015.

* cited by examiner (a)          (b)

MANUFACTURING METHOD OF MESOPOROUS INORGANIC OXIDE AND MESOPOROUS INORGANIC OXIDE MADE BY THE SAME

CROSS-REFERENCE TO RELATED APPLICATIONS

This application is the U.S. national stage application of International Patent Application No. PCT/KR2015/009988, filed Sep. 23, 2015, which claims priority to Korean Application Nos. 10-2014-0164980, filed Nov. 25, 2014 and 10-2015-0066276, filed May 12, 2015, the disclosures of each of which are incorporated herein by reference in their entirety.

TECHNICAL FIELD

The present invention relates to a method for manufacturing a mesoporous inorganic oxide and a mesoporous inorganic oxide manufactured by the method. More specifically, it relates to a method for manufacturing a mesoporous inorganic oxide which can be used as a carbon dioxide absorbent and the like at room temperature, and a mesoporous inorganic oxide manufactured by the method.

BACKGROUND ART

Various methods for manufacturing an inorganic oxide that contains a medium-sized pores or mesopores are known. In general, a micropore is defined as a pore having a diameter of less than 2 nm, ae mesopore is defined as a pore having a diameter of from 2 nm to 50 nm, and a macropore is defined as a pore having a diameter of greater than 50 nm. Inorganic oxides can be used as a catalyst, a catalyst auxiliary, or an adsorbent. In addition, inorganic oxides may be combined with zeolite.

Alkali metal-based oxides or alkaline earth metal-based oxides that are typical examples of such inorganic oxides have been in the spotlight as an absorbent for capture and storage of carbon dioxide. In recent years, metal oxide nanoparticles are widely used in an adsorbent, a catalyst, a sensor, and the like since they have a high ratio of surface area to volume. Among them, MgO is considered as a promising catalyst and a promising adsorbent for environmental contaminants.

MgO reacts with $CO_2$ to be converted into $MgCO_3$. However, a low ratio of surface area to volume and the carbonate layer formed on the surface are a barrier when an alkaline earth metal-oxide such as MgO undergoes an additional reaction with $CO_2$. Hence, a measure for increasing the adsorption efficiency of an alkali metal-based or alkaline earth metal-based $CO_2$ adsorbent is required.

As an effective method for increasing the $CO_2$ adsorption efficiency of an alkali metal-based or alkaline earth metal-based oxide, there is a method to expose more active sites by decreasing the particle size.

From this point of view, a method for manufacturing a nanostructure of magnesium oxide is disclosed in Non-Patent Document 1. According to this method, magnesium acetate tetrahydrate as the metal source, ammonium oxalate monohydrate as the capping ligand, and a surface active agent are mixed, heated for 24 hours at 40° C., and then aged for 100 hours at 80° C. Thereafter, the mixture is filtered, washed, dried, and then sintered for 4 hours at 850° C., thereby synthesizing a porous MgO nanostructure having a specific surface area of 47 $m^2g^{-1}$ and a pore diameter of 24 nm.

According to the method of Non-Patent Document 1, a mesoporous material is manufactured through a multi-step reaction, thus the manufacturing process is complicated and requires a long period of time of about one week, and the mass production is difficult, the surface active agent and the like that are used generate secondary environmental contaminants, and it is economically infeasible. In addition, the specific surface area or the pore diameter falls short of the expected level.

Hence, it is urgent to supply an inorganic oxide which saves energy by being manufactured as a mesoporous inorganic oxide at a relatively low temperature, is economically feasible as the manufacturing process is simplified, is environmentally friendly, and leads to an optimized efficiency in an adsorbent, a catalyst, a sensor, and the like as a process for mass production is developed.

CITATION LIST (Non-Patent Document 1) A. Tadjarodi, M. Sedghi, K. Bijanzad, Journal of NanoStructures 2 (2012) 273-278

DISCLOSURE OF THE INVENTION

Technical Problem

One aspect of the present invention is intended to propose a method for manufacturing an environmentally friendly mesoporous inorganic oxide, in which the manufacturing process is simplified to increase the economical feasibility.

Another aspect of the present invention is intended to propose a mesoporous inorganic oxide having a high specific surface area as the particle size is dramatically decreased.

However, problems to be solved by the present invention are not limited to the problem mentioned above, and other problems which have not been mentioned will be clearly understood by those skilled in the art from the following description.

Technical Solution

In order to achieve the above object, one aspect of the present invention provides a method for manufacturing a mesoporous inorganic oxide, which includes preparing a mixture of an amorphous inorganic oxide and a metal salt, the metal salt selected from the group consisting of at least one kind of alkali metal-containing compound, at least one kind of alkaline earth metal-containing compound, and any combination thereof; sintering the mixture of the metal salt and the amorphous inorganic oxide; and removing the metal salt contained in the sintered mixture.

Another aspect of the present invention provides a mesoporous inorganic oxide that is manufactured by the above method and is composed of an aggregate of inorganic oxide particles having a size of from 2 nm to 5 nm.

Advantageous Effects

The method for manufacturing a mesoporous inorganic oxide according to the present invention has a simplified manufacturing process, has a short period of manufacturing time of about 1 day, does not generate secondary environmental contaminants to be environmentally friendly, and enables mass production, and the mesoporous inorganic oxide manufactured by the method for manufacturing a mesoporous inorganic oxide according to the present invention has a dramatically decreased particle size and thus has an increased specific surface area and increased active sites.

BEST MODE FOR CARRYING OUT THE INVENTION

Hereinafter, exemplary embodiments of the present invention will be described in detail with reference to the accompanying drawings so as to be easily carried out by those skilled in the art. However, it should be noted that the present invention is not limited to the following exemplary embodiments and may be implemented in various forms.

Throughout the present specification, when a portion "includes" a component, it means that the portion does not exclude other components but may include other components unless otherwise there is a description to be opposite to this. The terms of degree such as "approximately", "about", and "substantially" used throughout the present specification are used as the meaning of the presented numerical value or close to the presented numerical value when an intrinsic allowable error of the manufacture and material is presented, and they are used in order to prevent the unscrupulous infringer from exploiting the disclosure having an accurate or absolute numerical value presented in order to facilitate understanding of the present invention. The terms "step of -ing" or "step of -" used throughout the present specification does not mean the "step for -".

Throughput the present specification, the term "any combination thereof" included in the expression of Markush form means one or more mixtures or combinations selected from the group consisting of the components described in the expression of Markush form, and thus it includes one or more selected from the group consisting of the components.

In the present specification, the term "consists of", "includes", or the like should not be construed as necessarily includes all of the various components or steps described in the specification but should be construed as may not include some components or some steps or may further include additional components or additional steps.

The present invention relates to a method for manufacturing a mesoporous inorganic oxide and a mesoporous inorganic oxide manufactured by the method. More specifically, it relates to a method for manufacturing a mesoporous inorganic oxide capable of being used as a carbon dioxide absorbent and the like at room temperature, by which a mesoporous inorganic oxide having a large specific surface area can be produced from an amorphous inorganic oxide having a low specific surface area in a large amount at low cost while simplifying the manufacturing process unlike a usual manufacturing method.

Figure 1:
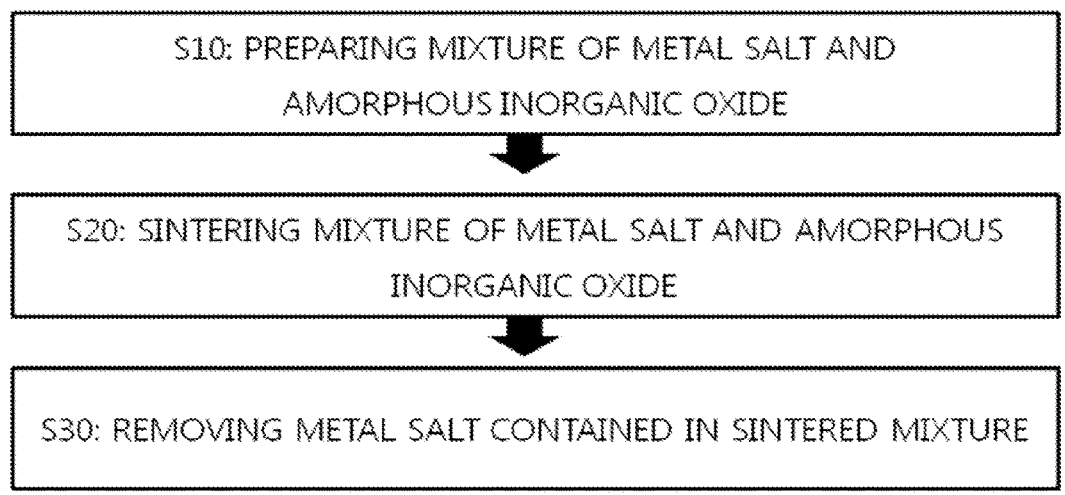
FIG. 1 is a process diagram illustrating the method for manufacturing a mesoporous inorganic oxide according to Example of the present invention.

Hereinafter, the method for manufacturing a mesoporous inorganic oxide of the present invention will be described with reference to FIG. 1.

First, a mixture of a metal salt and an amorphous inorganic oxide is prepared (S10).

The mixture of a metal salt and an amorphous inorganic oxide may be prepared by (1) a liquid-phase method or (2) a solid-phase method.

In the liquid-phase method, a metal salt solution is prepared by dissolving the metal salt in a solvent that can dissolve the metal salt, the amorphous inorganic oxide is impregnated with the metal salt solution, and the resultant is stirred for a certain period of time so that the inorganic oxide functions as a support and the metal salt is attached to the surface of the support. The amount of the metal salt component to be impregnated is preferably smaller than the saturation amount of the metal salt that is the limit in which the metal salt dissolves in the solvent. This is because the metal salt can be evenly dispersed in the support when the amount of the metal salt to be impregnated is properly controlled.

In the present invention, the kind of solvent is not particularly limited, and any solvent that is commonly used in the art may be used. Specifically, the solvent may be selected from water such as distilled water or deionized water, an alcohol, dimethylformamide (DMF), or any combination thereof, but it is not limited thereto, and any one may be used as long as it can dissolve the metal salt compound and evaporate at a low temperature of 50° C. or lower to be removed.

Examples of the alcohol may include methanol, ethanol, propanol, isopropanol, n-butanol, iso-butanol, sec-butanol, tert-butanol, n-pentanol, iso-pentanol, sec-pentanol, tert-pentanol, hexanol, heptanol, octanol, nonanol, decanol, undecanol, dodecanol, and pentadecanol, but the alcohol is not limited thereto. Examples thereof may also include polyols such as ethylene glycol, glycerol, erythritol, xylitol, and mannitol, but the alcohol is not limited thereto.

The solvent used is removed after the inorganic oxide is impregnated with the mixed solution of the metal salt compound and the solvent, a common solvent removing method may be used for this. For example, a process of evaporating the solvent for from 6 to 12 hours at a temperature of 50° C. or lower may be conducted one time or a plurality of times. In addition, the drying may be conducted by drying the solvent for 24 hours or longer at from 55° C. to 65° C. using a vacuum evaporator. A change in composition of the inorganic oxide and the metal salt impregnated into the inorganic oxide is prevented when the removal and drying of the solvent is conducted at a relatively mild condition as described above, thus the metal salt impregnated into the inorganic oxide can melt at a low temperature of from 200° C. to 400° C. during the subsequent sintering process, and as a result, it is possible to easily manufacture a mesoporous inorganic oxide capable of constantly maintaining the structure of the pores in a large amount.

Meanwhile, the method for preparing the mixture of a metal salt and an amorphous inorganic oxide by the solid-phase method can be simply achieved through a process of simply mixing a metal salt compound in a solid state with an amorphous inorganic oxide in a solid state in a solid phase.

The metal salt is one which can melt at a temperature at which the subsequent sintering process is conducted, and the metal salt may be selected from the group consisting of at least one kind of alkali metal-containing compound, at least one kind of alkaline earth metal-containing compound, and any combination thereof, but it will be limited thereto.

The metal salt compound as described above has a melting temperature of from 200° C. to 400° C., and thus it is suitable for forming mesopores by mixing it with an inorganic oxide in the present invention.

The alkali metal-containing compound may be a salt containing a metal selected from lithium (Li), sodium (Na), potassium (K), rubidium (Rb), cesium (Cs), or any combination thereof. In addition, the alkaline earth metal-containing compound may be a salt containing a metal selected from magnesium (Mg), calcium (Ca), strontium (Sr), barium (Ba), or any combination thereof.

The salt may be selected from a nitrite ($NO^{2-}$), a nitrate ($NO^{3-}$), a carbonate ($CO_3^{2-}$), a sulfate ($SO_4^{2-}$), a phosphate ($PO_4^{3-}$), or any combination thereof, but it is not limited thereto. Examples thereof may also include a halide, a hydroxide, chlorinate, a carboxylate, and an acetate.

Hence, specific examples of the alkali metal-containing compound or the alkaline earth metal-containing compound in the present invention may include lithium nitrate, lithium carbonate, sodium nitrate, sodium carbonate, potassium nitrate, potassium carbonate, calcium nitrate, and calcium carbonate.

The metal salt compound may be a eutectic mixture.

The eutectic mixture is a solid composed of two or more components and refers to a solid mixture which has a constant melting point as if one kind of solid compound and of which the liquid phase formed by melting has the same composition as the original solid phase. In addition, the melting point of the eutectic mixture is referred to as the eutectic point.

The reason why a eutectic mixture of a metal salt is adopted in order to introduce pores into an inorganic oxide in the present invention is because the eutectic point may be lower than the individual melting points of the compounds when two or more compounds having the eutectic point are mixed, thus it is possible to melt the mixture using lower energy than that used for melting the individual compounds, and this makes it possible to conduct the desired pore-forming process by a low-temperature and low-energy process. Hence, the eutectic point can be controlled by controlling the kind and mixing ratio of the components constituting the eutectic mixture, as a result, the sintering temperature can be variously controlled, the pore shape of the inorganic oxide can be diversified, and thus it is believed that the reactivity of the mesoporous inorganic oxide can also be controlled in association with the control of the specific surface area and active sites thereof.

The eutectic point may be appropriately formed in a middle-high temperature region when such a compound constitutes a eutectic mixture.

Hence, the eutectic mixture may be a single alkali metal-containing compound, a mixture of two or more kinds of alkali metal-containing compounds, a single alkaline earth metal-containing compound, a mixture of two or more kinds of alkaline earth metal-containing compounds, or a mixture of one or more kinds of alkali metal-containing compounds and one or more kinds of alkaline earth metal-containing compounds. The eutectic point can be controlled by controlling the components of the mixture and the mixing ratio of the components.

The inorganic oxide that is used in the mixture of a metal salt and an amorphous inorganic oxide may be selected from magnesia (MgO), AlMgO, silica ($SiO_2$), alumina ($Al_2O_3$), titania ($TiO_2$), zirconia ($ZrO_2$), tin oxide, cobalt oxide, zinc oxide, indium oxide, nickel oxide, hafnium oxide, vanadium oxide, or any combination thereof, but the inorganic oxide is not limited thereto. MgO is even more preferable.

The amorphous inorganic oxide may be a commercially available inorganic oxide which does not have a constant shape but has a specific surface area of 100 $m^2g^{-1}$ or less.

The mixture of the metal salt and the amorphous inorganic oxide is sintered after the mixture of the metal salt and the amorphous inorganic oxide is prepared (S20).

The metal salt in the mixture is melted and the crystal structure of the amorphous inorganic oxide is rearranged through the sintering process.

The step of sintering may be conducted in an air, nitrogen, helium, hydrogen, water vapor, or reducing gas atmosphere, but the atmosphere is not limited thereto, and gas flow rate is preferably 60 ml/min or more. In addition, the sintering temperature in the step of sintering is required to be higher than the melting temperature of the metal salt and lower than the decomposition temperature of the metal salt. In other words, it is intended to cause the recrystallization of the metal oxide in a state in which the metal salt is molten. A metal salt compound has a melting temperature of from 200° C. to 400° C., and it may be decomposed at a temperature of from 600° C. to 700° C., and thus the sintering step is conducted at a temperature of about from 400° C. to 700° C. and preferably from 400° C. to 600° C. The sintering may be conducted about from 2 hours to 7 hours, but it is not limited thereto. The effect of recrystallization of the structure of the mesoporous inorganic oxide is expected when the sintering is conducted in the above range.

The metal salt contained in the sintered mixture is removed after the sintering is completed (S30).

As the method for removing the metal salt, a method in which the metal salt compound is treated with a solvent in which the metal salt compound can dissolve so as to be removed. The solvent that can be used at this time is not particularly limited as described above, and any solvent that is commonly used in the art may be used. Specifically, the solvent may be selected from water such as distilled water or deionized water, an alcohol, dimethylformamide (DMF), and any combination thereof, but it is not limited thereto, and any one may be used as long as it can dissolve the metal salt compound and evaporate at a low temperature of 50° C. or lower to be removed.

When the metal salt is removed from the sintered mixture in this manner, the space that has been occupied by the metal salt remains to be a pore and the rearranged inorganic oxide particles remain to form a frame, whereby an inorganic oxide equipped with a mesopore is obtained.

It is possible to reuse the removed metal salt through recycling.

Figure 2:
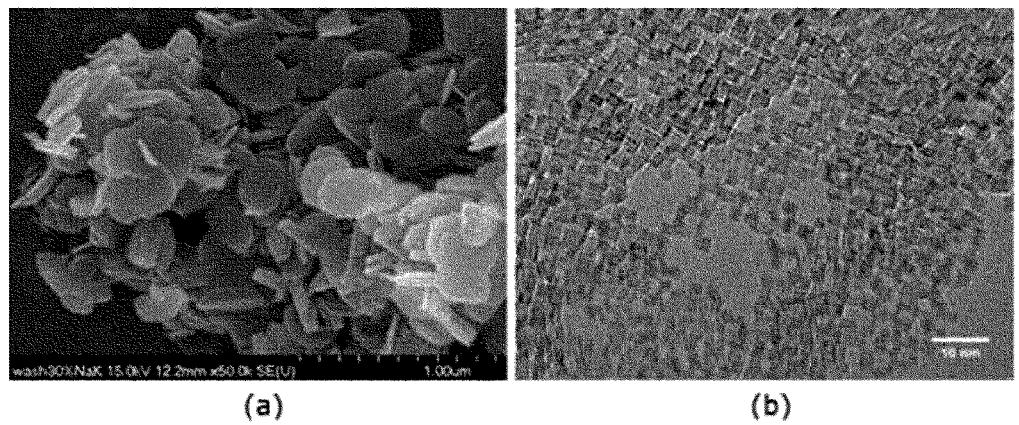
FIG. 2 is images of mesoporous magnesium oxide manufactured according to Example of the present invention taken using a scanning electron microscope (SEM) (a) and a transmission electron microscope (TEM) (b).

FIG. 2 illustrates an image of mesoporous MgO manufactured by the method that has been described above in detail. FIG. 2 (a) is an image taken using a SEM and a great number of nanoplate structures are observed in the image. FIG. 2 (b) is an image taken using a TEM, and in the image, the size of the crystal particles of MgO is about from 2 nm to 5 nm, these nanocrystal particles are present in the form of an aggregate, and mesopores are observed together with them. This indicates that the size is significantly decreased as compared to the inorganic oxide particles manufactured by the prior art, and thus an increase in active sites is expected.

In this manner, the manufacture of the mesoporous inorganic oxide of the present invention can be completed in a short period of time of about 1 day, and thus it is possible to dramatically shorten the process time of about one week in the prior art. In addition, it is possible to introduce mesopores having a large specific surface area into a commercial inorganic oxide by a relatively simple process, and when using the mesoporous inorganic oxide as an air pollutant absorbent, an active component can be favorably distributed in the absorbent particles so as to increase the utilization/reactivity of the active component and to facilitate the adsorption/absorption of air pollutants required for the reaction.

The mesoporous inorganic oxide manufactured by the manufacturing method of the present invention may be composed of aggregates of inorganic oxide particles having size of from 2 nm to 5 nm, may have a specific surface area of from 100 to 400 $m^2g^{-1}$ and a pore volume of from 0.3 to 1.0 $ccg^{-1}$, and thus is expected to be highly utilizable in an absorbent for air pollutants such as carbon dioxide, a catalyst, a sensor, and the like. The data of specific surface area and pore volume are a result that is obtained by measuring and confirming them through the experiment that is repeated several times using various samples.

Hereinafter, the present invention will be described in detail by way of Examples. However, the following Examples are only examples for explaining the present invention in more detail but are not intended to limit the scope of the present invention.

EXAMPLES

Example 1

Manufacture of Mesoporous MgO Using Liquid-phase Method

A commercially available amorphous MgO having a specific surface area of 100 $m^2g^{-1}$ or less was introduced into a solution prepared by dissolving a eutectic mixture consisting of $NaNO_3$ and $KNO_3$ or $NaNO_3$ in water of the solvent and stirred, and water was then evaporated for 3 hours at a temperature of 50° C. using a rotary evaporator. After water was removed, the resultant was dried for 12 hours in an oven at 60° C. Thereafter, the dried substance was sintered at a temperature of 400° C. in the air (oxygen) atmosphere by heating. After sintering was completed, an excess amount of distilled water to be 100 times or more the volume of the mixture was added to the resultant to completely remove the metal salt by dissolving. At this time, a filtration step may be added.

Mesoporous MgO thus manufactured is defined as L-Meso-Na—K—MgO or L-Meso-Na—MgO for convenience.

Example 2

Manufacture of Mesoporous MgO Using Solid-phase Method

A commercially available amorphous MgO having a specific surface area of 100 $m^2g^{-1}$ or less was completely mixed with a eutectic mixture consisting of $NaNO_3$ and $KNO_3$ or $NaNO_3$ without using water of the solvent. Thereafter, the mixture was sintered at a temperature of 400° C. in the air (oxygen) atmosphere by heating. After sintering was completed, an excess amount of distilled water to be 100 times or more the volume of the mixture was added to the resultant to completely remove the metal salt by dissolving. At this time, a filtration step may be added.

The absorbent thus manufactured is defined as S-Meso-Na—K—MgO or S-Meso-Na—MgO for convenience.

Analysis Example

Analysis on Surface Properties of Manufactured MgO

The analytical results on the surface properties of each of magnesium oxide manufactured in Example 1 and Example 2 are presented in the following Table 1.

TABLE 1

| | BET surface area ($m^2g^{-1}$) | Pore volume ($ccg^{-1}$) | t-plot micropore area ($m^2g^{-1}$) | t-plot external surface area ($m^2g^{-1}$) |
|---|---|---|---|---|
| MgO | 20.7 | 0.062 | 8.51 | 12.2 |
| L-Meso-Na—K—MgO (before removing metal salt) | 28.3 | 0.085 | 7.27 | 20.1 |
| S-Meso-Na—K—MgO (before removing metal salt) | 12.0 | 0.048 | 4.83 | 7.12 |
| L-Meso-Na—K—MgO (after removing metal salt) | 282 | 0.647 | 24.5 | 258 |
| S-Meso-Na—K—MgO (after removing metal salt) | 291 | 0.293 | — | 402 |

Figure 3:
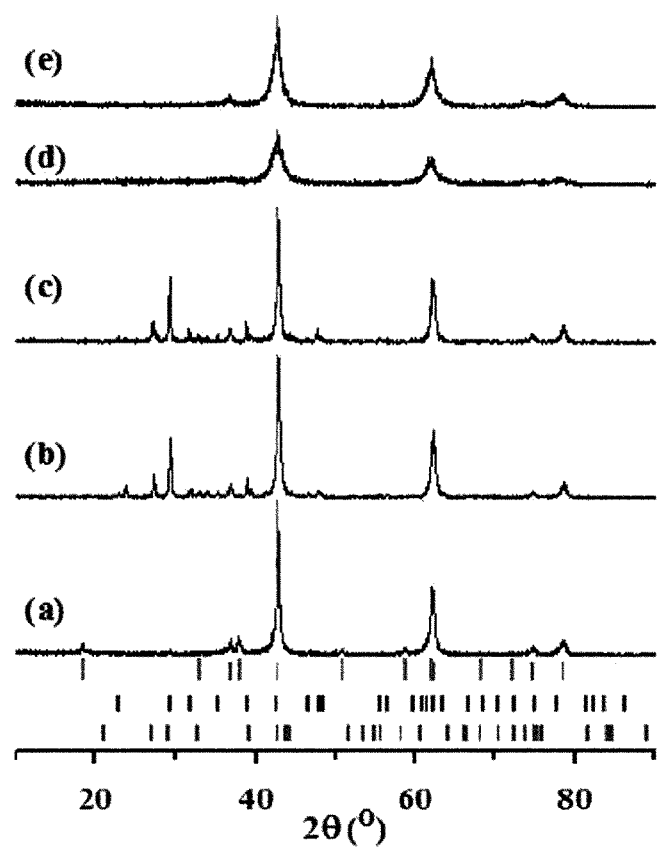
FIG. 3 is X-ray diffraction (XRD) spectra of mesoporous magnesium oxide (b, c, d, and e) manufactured according to Example of the present invention and commercial MgO (a).

FIG. 3 is X-ray diffraction (XRD) spectra of mesoporous magnesium oxide, (b) L-Meso-Na—K—MgO (before removing metal salt), (c) S-Meso-Na—K—MgO (before removing metal salt), (d) L-Meso-Na—K—MgO (after removing metal salt), and (e) S-Meso-Na—K—MgO (after removing metal salt) which are manufactured according to Example of the present invention and all have been subjected to the sintering process, and (a) commercial MgO.

From the results of X-ray diffraction spectra, it can be seen that commercial magnesium oxide is composed of larger particles and has the diffraction line with a small line width, but those treated with molten metal salt have an increased line width, and thus it is believed that the particle size has decreased. In addition, it can be seen that metal salt-supported magnesium oxide exhibits diffraction characteristics of the metal salt.

Application Example 1

Knoevenagel Condensation Reaction

L-Meso-Na—K—MgO manufactured in Example 1 and commercial MgO were used as a catalyst to compare the reactivity thereof.

Before conducting the reaction, the MgO samples were activated for 6 hours in a vacuum of 623 K. The Knoevenagel condensation reaction of benzaldehyde with ethyl cyanoacetate was conducted using a 35 ml glass reactor Chemistation PPS-2510. Benzaldehyde (10.0 mmol), ethyl cyanoacetate (10.0 mmol), and the catalyst (catalyst/reactant=0.03, mass fraction) were added to 5.0 mL of ethanol (Aldrich) of the solvent. The reaction was conducted at 80° C. and the product was obtained.

The reaction scheme is represented by Reaction Formula 1.

[Reaction Formula 1]

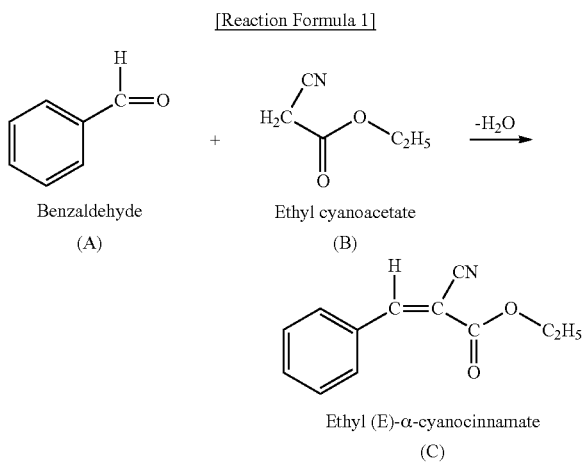

Benzaldehyde (A)    Ethyl cyanoacetate (B)

Ethyl (E)-α-cyanocinnamate (C)

Figure 7:
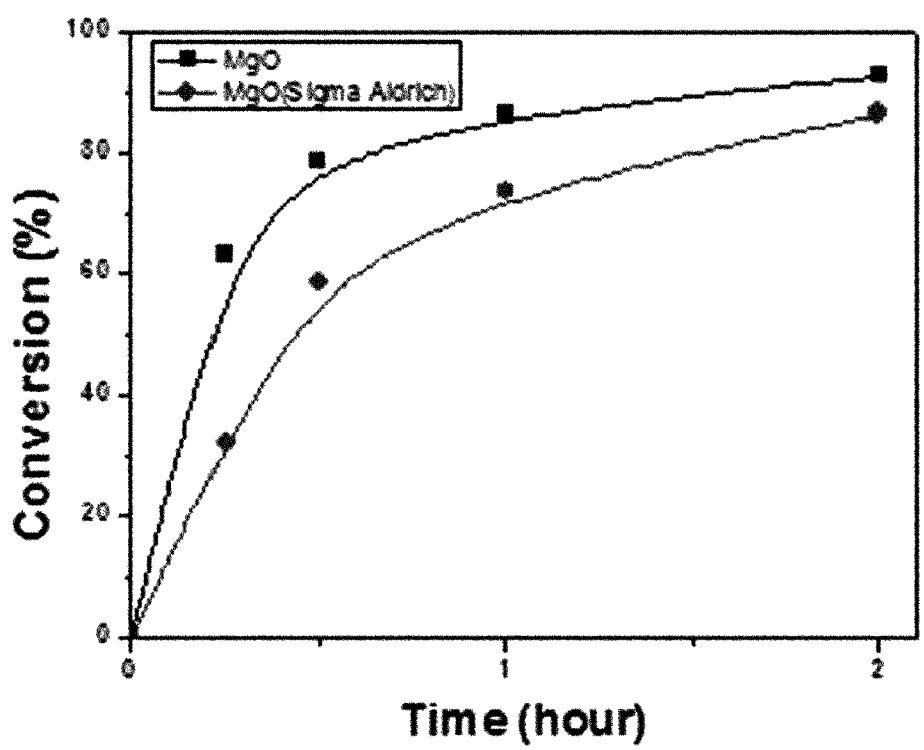
FIG. 7 is a graph illustrating the percent conversion of benzaldehyde into a product of the Knoevenagel condensation reaction when commercial MgO (●) and mesoporous magnesium oxide (■) manufactured according to Example of the present invention are used as a catalyst.

The percent conversion of benzaldehyde (A) of the reactant into ethyl (E)-α-cyanocinnamate (C) of the product according to the reaction is illustrated in FIG. 7 to compare. The percent conversion of benzaldehyde (A) into the product of the Knoevenagel condensation reaction is significantly higher in the case of using mesoporous magnesium oxide (■) manufactured according to Example of the present invention as a catalyst as compared to commercial MgO (●), and such a result indicates that mesoporous MgO manufactured according to the present invention is highly utilizable as a catalyst.

Application Example 2

Carbon Dioxide Absorbent

The performance to absorb carbon dioxide of L-Meso-Na—K—MgO manufactured in Example 1 and S-Meso-Na—K—MgO manufactured in Example 2 was measured without additionally supporting an active component.

Figure 4:
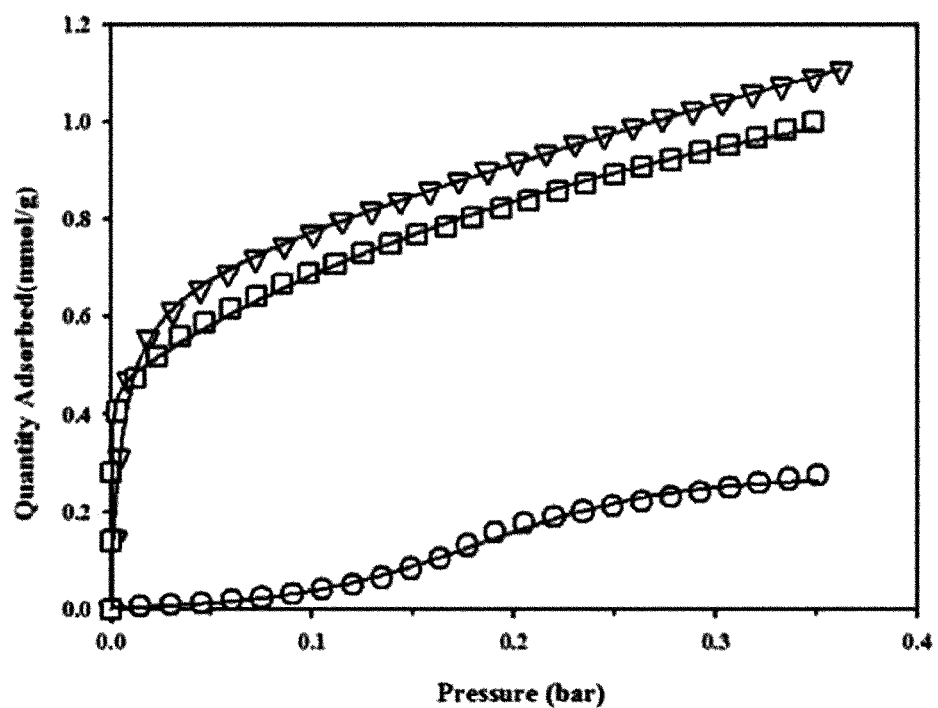
FIG. 4 is a graph illustrating the isotherms of carbon dioxide adsorption on commercial MgO (○) and mesoporous magnesium oxide (□ and ▽) manufactured according to Example of the present invention at 0° C.
Figure 5:
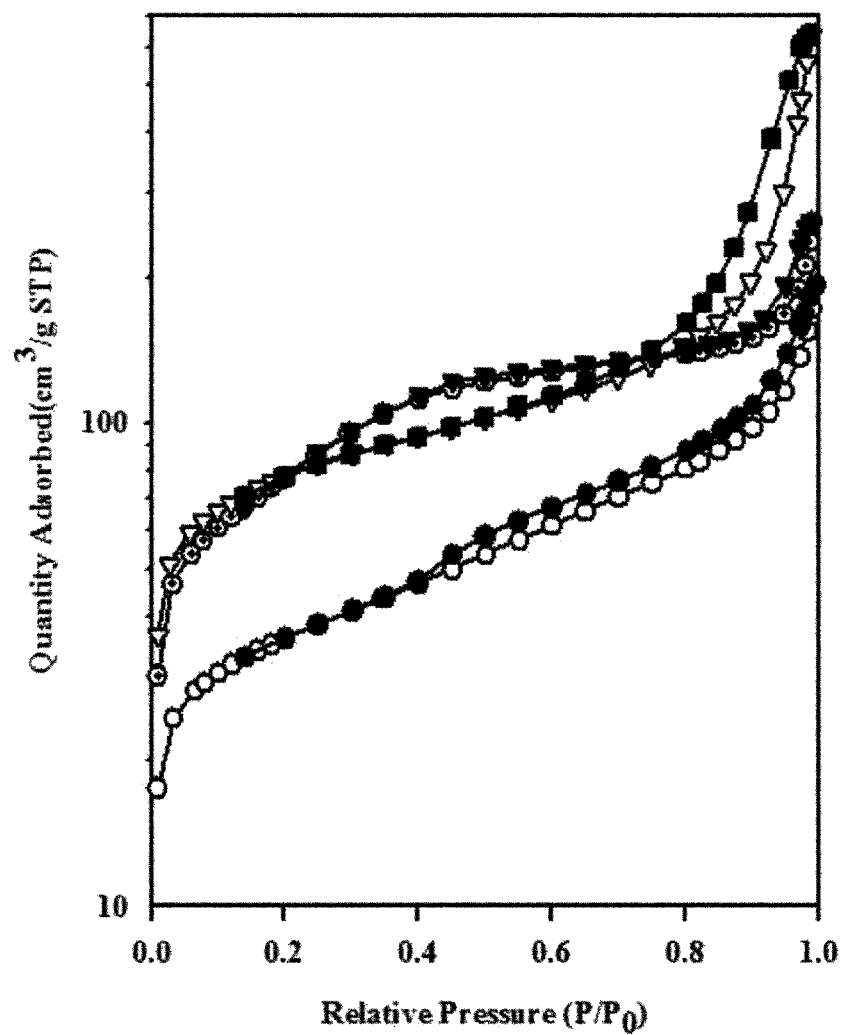
FIG. 5 a graph illustrating the isotherms carbon dioxide adsorption on mesoporous magnesium oxide (□, ■, ▽, and ▼) manufactured according to Example of the present invention and commercial MgO (○ and ●).

FIG. 4 and FIG. 5 are graphs illustrating the isotherms of carbon dioxide adsorption on commercial MgO (○ and ●) and mesoporous magnesium oxide, L-Meso-Na—K—MgO (□ and ■) and S-Meso-Na—K—MgO (∇ and ▼), manufactured according to Example of the present invention at 0° C.

It can be seen that the performance to adsorb carbon dioxide of the MgO samples according to the present invention is superior to that of commercial MgO.

Figure 6:
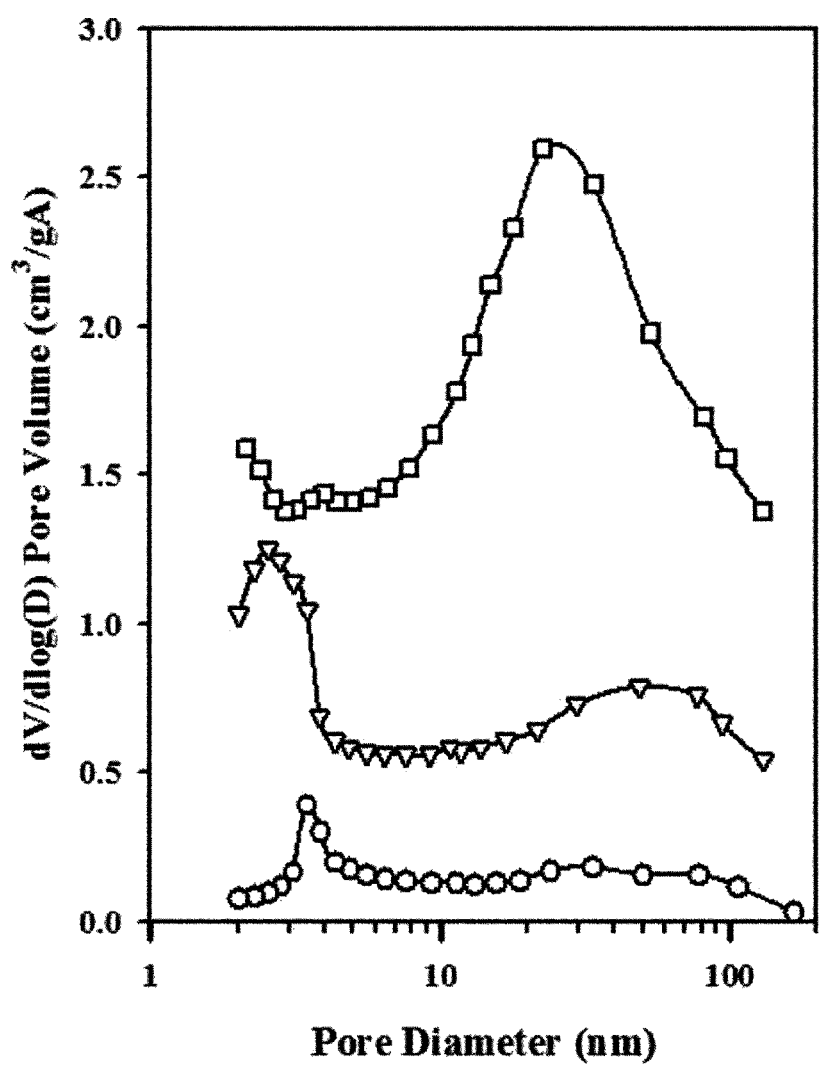
FIG. 6 is a graph illustrating the pore diameter and pore volume of commercial MgO (○) and mesoporous magnesium oxide (□ and ▽) manufactured according to Example of the present invention.

FIG. 6 relates to the pore size, and it indicates that the pore volume can be controlled depending on the process of mixing the metal salt and magnesium oxide at the time of manufacture. It can be seen that the pore size is controlled to be smaller in L-Meso-Na—K—MgO (□) mixed in a liquid phase than in S-Meso-Na—K—MgO (∇) mixed in a solid phase.

INDUSTRIAL APPLICABILITY

The present invention is significantly useful in that a method for manufacturing a mesoporous inorganic oxide which has a simplified manufacturing process, has a short period of manufacturing time of about 1 day, does not generate secondary environmental contaminants to be environmentally friendly, and enables mass production is provided and a mesoporous inorganic oxide which has a dramatically decreased particle size and thus has an increased specific surface area and increased active sites is provided.

What is claimed is:

1. A method for manufacturing a mesoporous inorganic oxide, the method comprising:
   preparing a mixture of an amorphous inorganic oxide and a metal salt, the metal salt being at least one kind of alkali metal-containing salt, at least one kind of alkaline earth metal-containing salt, or any combination thereof;
   sintering the mixture of the metal salt and the amorphous inorganic oxide; and
   removing the metal salt contained in the sintered mixture,
   wherein the mixture of the metal salt and the amorphous inorganic oxide is prepared by mixing the metal salt and the amorphous inorganic oxide in a solid phase.

2. The method according to claim 1, wherein the mixture of the metal salt and the amorphous inorganic oxide is prepared by impregnating the amorphous inorganic oxide with a metal salt solution prepared by dissolving the metal salt in a solvent and then removing the solvent.

3. The method according to claim 1, wherein the inorganic oxide is magnesia (MgO), silica ($SiO_2$), alumina ($Al_2O_3$), titania ($TiO_2$), zirconia ($ZrO_2$), tin oxide, cobalt oxide, zinc oxide, indium oxide, nickel oxide, hafnium oxide, vanadium oxide, or any combination thereof.

4. The method according to claim 1, wherein the metal salt is a eutectic mixture.

5. The method according to claim 1, wherein the metal salt comprises nitrite ($NO^{2-}$), nitrate ($NO^{3-}$), carbonate ($CO_3^{2-}$), sulfate ($SO_4^{2-}$), phosphate ($PO_4^{3-}$), or any combination thereof.

6. The method according to claim 1, wherein the alkali metal-containing salt contains lithium (Li), sodium (Na), potassium (K), rubidium (Rb), cesium (Cs), or any combination thereof.

7. The method according to claim 1, wherein the alkaline earth metal-containing salt contains magnesium (Mg), calcium (Ca), strontium (Sr), barium (Ba), or any combination thereof.

8. The method according to claim 1, wherein a sintering temperature in the sintering of the mixture is higher than a melting temperature of the metal salt and lower than a decomposition temperature of the metal salt.

9. The method according to claim 1, wherein the sintering of the mixture of the metal salt and the amorphous inorganic oxide is performed at a temperature of 400° C. to 600° C.

10. The method according to claim 1, wherein the removing of the metal salt comprises:
    removing the metal salt by dissolving the metal salt in a solvent.

11. The method according to claim 1, wherein a specific surface area of the amorphous inorganic oxide is 100 $m^2g^{-1}$ or less.

12. The method according to claim 2, wherein the solvent is water, an alcohol, dimethylformamide (DMF), or any combination thereof.

13. The method according to claim 10, wherein the solvent is water, an alcohol, dimethylformamide (DMF), or any combination thereof.

14. The method according to claim 2, wherein the removal of the solvent is carried out by performing a process of evaporating the solvent for from 6 to 12 hours at a temperature of 50° C. or lower one time or a plurality of times.

15. The method according to claim 2, wherein the removal of the solvent is performed by drying the solvent for 24 hours or longer at from 55° C. to 65° C.

16. A mesoporous inorganic oxide comprising:
   an aggregate of inorganic oxide particles having a size of from 2nm to 5nm,
   wherein the mesoporous inorganic oxide is manufactured by the method according to claim 1.

17. The mesoporous inorganic oxide according to claim 16, wherein a specific surface area of the mesoporous inorganic oxide is from 100 $m^2g^{-1}$ to 400 $m^2g^{-1}$ and a pore volume of the mesoporous inorganic oxide is from 0.3 $ccg^{-1}$ to 1.0 $ccg^{-1}$.

* * * * *